Figure 1:
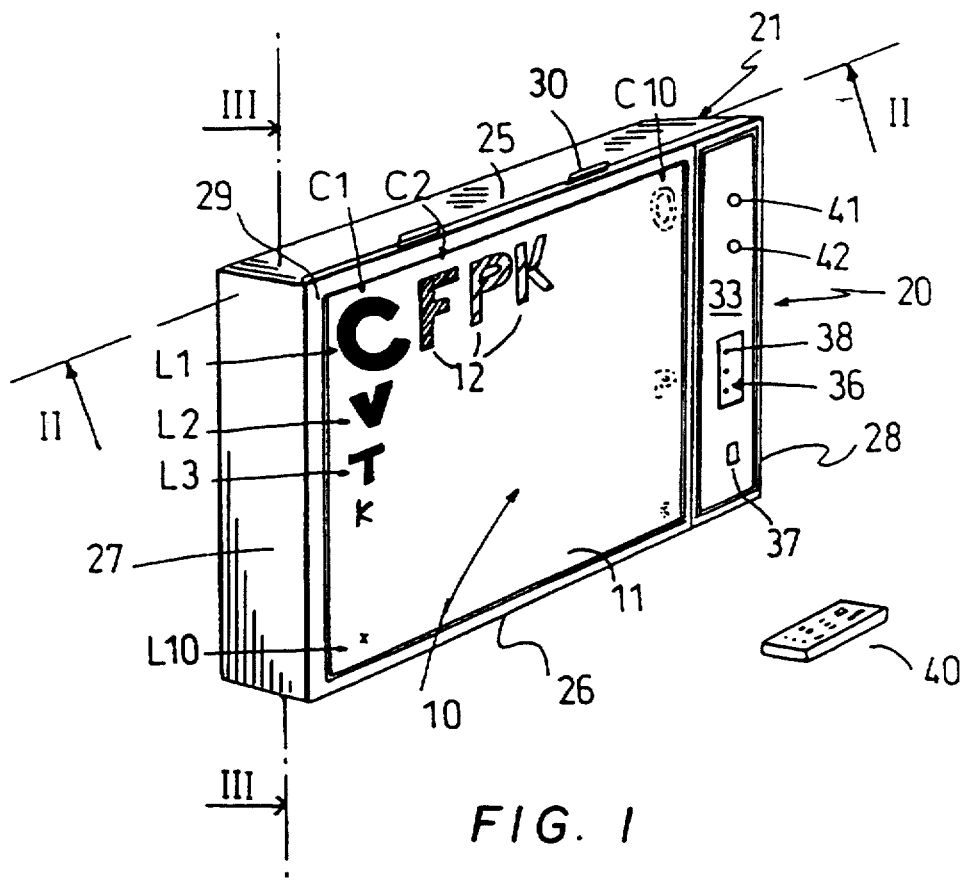

United States Patent [19]
Pynson

[11] Patent Number: 5,430,510
[45] Date of Patent: Jul. 4, 1995

[54] EQUIPMENT FOR TESTING VISUAL ACUITY AND/OR SENSITIVITY TO SPATIAL CONTRASTS IN HUMANS, AND A CORRESPONDING DEVICE AND MANUFACTURING PROCESS

[75] Inventor: Joël Pynson, Paris, France

[73] Assignee: OPSIA, Ramonville Saint Agne, France

[21] Appl. No.: 178,321

[22] PCT Filed: Jul. 24, 1992

[86] PCT No.: PCT/FR92/00739

§ 371 Date: Jan. 18, 1994

§ 102(e) Date: Jan. 18, 1994

[87] PCT Pub. No.: WO93/02614

PCT Pub. Date: Feb. 18, 1993

[30] Foreign Application Priority Data

Aug. 1, 1991 [FR] France .................. 91.09857

[51] Int. Cl.$^6$ ........................ A61B 3/02
[52] U.S. Cl. ........................ 351/239; 351/243
[58] Field of Search ........... 351/211, 237, 239, 243, 351/246; 128/665, 745; 606/204.25

[56] References Cited

U.S. PATENT DOCUMENTS

| | | | |
|---|---|---|---|
| 4,365,873 | 12/1982 | Ginsburg | 351/239 |
| 4,607,923 | 8/1986 | Task et al. | 351/239 |
| 4,615,594 | 10/1986 | Task | 351/239 |
| 4,789,234 | 12/1988 | Ginsburg et al. | 351/239 |
| 4,800,404 | 1/1989 | Ginsburg et al. | 351/243 |
| 4,968,131 | 11/1990 | Lewis | 351/239 |

FOREIGN PATENT DOCUMENTS

| | | |
|---|---|---|
| 2342051 | 9/1977 | France . |
| 2045457 | 10/1980 | United Kingdom . |
| 2064160 | 6/1981 | United Kingdom . |

OTHER PUBLICATIONS

"Augenheilkunde" Martin Reim—Stuttgart: Enke, 1985, ISBN 3-432-95401-9 2.17 Untersuchung der Kontrastwahrnehmung.

*Primary Examiner*—Anita Pellman Gross
*Assistant Examiner*—Huy Mai
*Attorney, Agent, or Firm*—Shlesinger Arkwright & Garvey

[57] ABSTRACT

Equipment for testing visual acuity and/or visual sensitivity to spatial contrasts in humans comprises a sheet having a plurality of optotypes disposed on one of its faces, the optotypes being distributed in rows $L_1 \ldots L_N$ and columns $C_1 \ldots C_N$. The optotypes having the same spatial frequency are arranged in the same row $L_1 \ldots L_N$, the spatial frequency increasing from the first row $L_1$ to the last row $L_1$, the spatial frequency corresponding with the spatial frequency used for acuity tests. The optotypes constituting contrast isosensitivity sets are arranged in columns $C_1 \ldots C_N$, and the luminance contrast of which has values decreasing from a first column $C_1$, with a maximum contrast value, to a last column $C_N$, with a minimum contrast value. N is an integer.

25 Claims, 3 Drawing Sheets

EQUIPMENT FOR TESTING VISUAL ACUITY AND/OR SENSITIVITY TO SPATIAL CONTRASTS IN HUMANS, AND A CORRESPONDING DEVICE AND MANUFACTURING PROCESS

The present invention concerns equipment for testing visual acuity and/or visual sensitivity to spatial contrasts in humans, and a corresponding device and a manufacturing process for such a test.

Contrasts perceived by humans may be of two types, ie temporal or spatial. Temporal contrasts correspond to variations in the contrast over time, as for example the variations in luminosity of a rotating warning light. Spatial contrasts on the other hand concern variations in contrast independently of time, but extending in space, ie for example a scene including areas of different contrasts, such as gradations of colours or different shades of grey (going for example from deep black to a grey which is barely tinted).

The present invention concerns solely a test for determining sensitivity to spatial contrasts in humans. In the following description it is thus understood that the term "contrast test" in fact means "spatial contrast tests".

Recent clinical studies have shown that it would certainly be beneficial to determine visual sensitivity to spatial contrasts even in subjects having good visual acuity. This is because certain pathological ocular conditions such as cataracts, glaucomas, disorders of the cornea, etc may be detected at a very early stage, by means of a contrast test, when the visual acuity function is still little affected or not affected at all. When detected quite early, such diseases may be treated more effectively. Likewise, this study of sensitivity to contrasts enables certain surgical techniques to be evaluated, such as corneal grafts, etc.

Devices enabling sensitivity to contrasts to be studied in humans are already known. The patent FR-2,342.051 (Acadia Associates) describes for example a device for determining sensitivity to contracts comprising a binocular viewing assembly, in which a patient sees transparencies appear which include as optotypes letters on a white background. By causing the background luminosity to vary, different absolute contrasts are created for all the letters carried by one transparency. The minimal contrast perceived by the patient is then determined for each size of letter (ie each spatial frequency of the optotype).

All these measurements are then entered on a graph indicating the minimum contrast perceived by the patient as a function of the spatial frequency. This curve is then compared with a standard curve established for a healthy subject. Any variations in the curve of the patient with respect to the standard curve reveal pathological ocular conditions etc.

One of the main drawbacks of such a device is that it requires considerable time to be spent on examination, in particular in order to produce and analyse the graphs. Such a device is far too time-consuming and complex to use for routine utilization, during a conventional ophthalmological screening examination. In addition, such a test disconcerts the patient and it is sometimes difficult to enable him to understand its operation, which has, of course, an adverse effect on the quality of the examination carried out.

Devices of the same type as the one described in U.S. Pat. No. 4,365.873 (Ginsburg), which is in the form of a transparent sheet having a plurality of test areas distributed in the form of rows and columns, are also already known. Each column has test areas with the same contrast and each row test areas with the same spatial frequency.

The patterns of the test areas are produced by networks, ie an alternation of dark and light areas with given contrasts and spatial frequencies. These dark and light areas may be sinusoidal or square in shape and are either vertical or sloping. The transparent sheet is placed on a diffusing face of a light box. The patient is placed at a certain distance from the box and has to indicate, for each of the test areas seen, whether its network is vertical or sloping.

The practitioner then notes the minimum contrast level discerned as a function of the spatial frequency of the test area discerned. It is then necessary to trace, for each patient, his curve of sensitivity to the contrasts as a function of the spatial frequencies. Such a device is also very time-consuming to set up. In addition, the patient is not very familiar with the networks presented in the test areas. Hence there is a danger that a test will not be understood, which may produce a completely false measurement of sensitivity to spatial contrasts.

In addition the devices known at present do not enable a patient's sensitivity to contrasts to be determined in conditions other than those of average illumination of about 80 to 90 cd/m$^2$. However, some patients complain of disorders occurring only in specific lighting conditions, ie at twilight or at a mesopic level (3 to 10 cd/m$^2$) or on very sunny days (high photopic level of about 600 to 1000 cd/m$^2$), or when dazzled (above 1000 cd/m$^2$).

The present invention aims to remedy all of these drawbacks and proposes equipment for easy testing of contrasts which does not disconcert the patient, is quick to carry out and enables a patient's contrast sensitivity function to be determined immediately as a function of spatial frequency, in order to reveal any pathological conditions or other ocular abnormalities. In addition, the contrast test according to the invention can also be used as a simple visual-acuity test.

Another aim of the present invention is to be able to carry out a test for sensitivity to spatial contrasts in humans in different lighting conditions, ie at a so-called twilight level, at an average level and at a level corresponding to strong sunlight, and even at a dazzling level.

To this end, the present invention concerns equipment for testing visual acuity and/or visual sensitivity to spatial contrasts in humans, of the type comprising a sheet provided on one of its faces with a plurality of optotypes distributed in the form of rows and columns, characterised in that the optotypes perceived by a person as having the same contrast value are arranged in the same column or row respectively and, moreover, the optotypes of the same spatial frequency corresponding to the one used for acuity tests are arranged in the same row or column respectively.

Thus the contrast test equipment according to the invention is in the form of a simple sheet with optotypes distributed in the form of rows and columns. It therefore resembles conventional visual acuity tests and does not disconcert the patient.

Advantageously, each column of optotypes has a contrast value perceived by the human eye as unique and decreasing from one column to the other, starting from a maximum contrast and continuing to the minimum contrast perceived by a healthy subject.

In addition, each of the rows has the same spatial frequency.

Advantageously, the spatial frequencies tested correspond directly to those used for traditional visual acuity tests. Thus the practitioner establishes, immediately and without having to draw a specific graph, the performance of his patient with respect to his sensitivity to spatial contrasts as a function of each spatial frequency corresponding to a degree of visual acuity. This performance can in fact be read directly from the sheet carrying the optotypes.

Conversely, the function of the rows and columns can be reversed. Thus each row can have optotypes with the same perceived contrast and each column can have optotypes with the same spatial frequency.

Preferably, the optotypes used are letters. Because of this, the patient tends to adapt without difficulty to this novel examination, which he understands easily because of its similarity with traditional acuity tests.

Advantageously, such a test is carried by a transparent or translucent sheet, to be placed on the diffusing face of a light box.

According to a variant embodiment, the optotypes shown are images or symbols which are easily recognisable by children or illiterates.

The present invention also aims to create a device using the acuity and/or contrast test equipment described above.

The objective of such a device is to make it possible to carry out a contrast test in a reliable and repeatable manner and under different luminosity conditions. The purpose here is to detect any abnormality in the perception of contrasts, both under normal luminosity and in twilight, sunlight, or even dazzling light.

To this end, the present invention concerns a device for determining visual acuity and/or sensitivity to contrasts in humans, of a type which includes acuity and/or contrast test equipment, characterised in that it comprises in combination:

- a means of supporting the acuity and/or contrast test equipment, having a diffusing front face adapted for carrying the said test,
- an illumination means housed inside the support means and adapted for illuminating uniformly, according to a predetermined luminosity, the front face of the support means, and
- the sheet of the said acuity and/or contrast test equipment placed on the front face of the support means, the said sheet comprising a plurality of rows and columns of optotypes, the optotypes perceived by a human as having the same contrast value are arranged in the same column or row respectively and, on the other hand, the optotypes of the same spatial frequency corresponding to the one used for acuity tests are arranged in the same row or column respectively.

Such a device thus has a means of supporting the contrast test equipment. An illumination means located inside the support makes it possible to illuminate uniformly a diffusing face of the support means, on which the acuity and/or contrast test equipment is placed. The resulting illumination is determined and makes it possible to implement the test according to the invention under controlled conditions of luminosity.

Preferably, such a device is equipped with means for selecting the appropriate illumination to make it possible to choose the luminosity conditions under which the test is carried out. These selection means control the current delivered to the light source.

Preferably, the light source comprises a plurality of neon tubes.

Such a light source is suitable for illuminating uniformly the whole of the diffusing face of the support means carrying the test equipment. Thus illumination levels are obtained on the diffusing face of about 3 to 10 $cd/m^2$ (twilight), 80 to 90 $cd/m^2$ (normal daylight) and 600 to 1000 $cd/m^2$ or even more (strong daylight).

The present invention also aims to create a method for carrying out the test according to the invention.

Such a method aims to create a test for visual acuity and/or sensitivity to spatial contrasts in humans, in which each optotype has a strictly defined, verifiable and adjustable contrast. Indeed, because of the low contrasts of some optotypes in the test equipment according to the invention, it is essential that the test equipment be reliable and provide true information and that the tests produced be strictly defined.

In addition, it is necessary to avoid any deterioration in the test over time, since that would have an adverse effect on the correct examination of the patient.

To this end, the present invention concerns a process for manufacturing equipment for testing visual acuity and/or sensitivity to contrasts, characterised in that it consists of:

- creating, by means of a central computing unit, optotypes of a size determined so as to confer on them a specific spatial frequency,
- giving the optotypes of a given size a density determined so as to confer on them a specific contrast value,
- arranging all the optotypes of the same spatial frequency in the same row or the same column,
- arranging all the optotypes perceived by a person as having the same contrasts in the same column or the same row,
- displaying the table of optotypes thus created on a screen associated with the central unit,
- producing a positive of the screen on a photosensitive film,
- producing a negative of the positive,
- printing the said negative on a sheet,
- verifying the contrast of each of the optotypes appearing on the print,
- deriving therefrom the optimum exposure times for the negative in order to obtain the required contrasts, and
- printing the said negative in order to produce a plurality of identical items of equipment for testing visual acuity and/or sensitivity to contrasts.

Such a manufacturing process makes it possible to control rigorously the contrast of each optotype created on the negative. Because of this, by modifying the times of exposure of the negative to light, it is possible to obtain precisely defined, reproducible contrast values for the final print. Thus the test equipment according to the invention has precisely defined optotypes and identical quality in all the test equipment produced. In addition, such test equipment does not tend to deteriorate over time under the effect of light.

Figure 2:
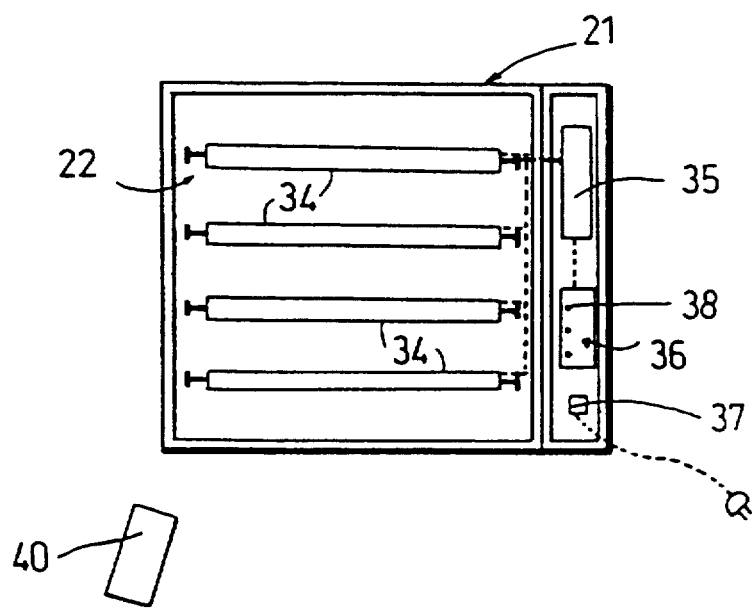
Figure 3:
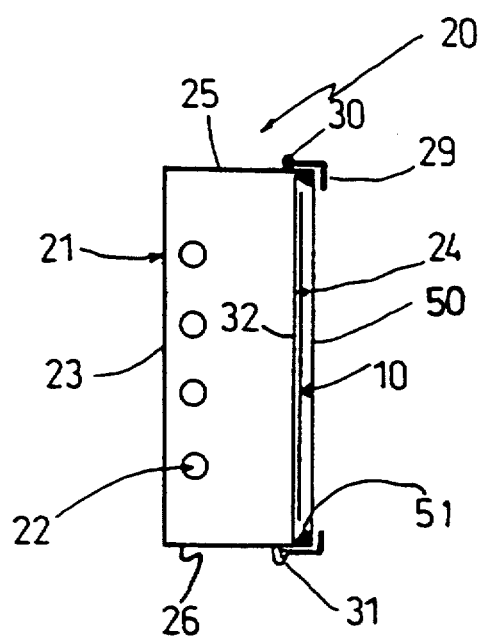
Figure 4:

Other objects, characteristics or advantages of the present invention will become clear from the following description with reference to the accompanying drawings in which:

FIG. 1 is a perspective view of a device for determining visual acuity and/or sensitivity to contrasts provided with test equipment according to the invention, FIG. 2 is a diagrammatic view of a cross section along the line II—II of FIG. 1, FIG. 3 is a cross section view of the device according to the invention, and FIG. 4 is an example of an embodiment according to a first variant of the test equipment according to the invention.

According to the embodiment shown in FIGS. 1 and 3, the equipment 10 for testing visual acuity and/or sensitivity to spatial contrasts according to the invention comprises a sheet 11 made of translucent material having on one of its faces a plurality of optotypes 12. These optotypes consist, in the example shown, of letters. The test equipment thus includes a plurality of rows $L_1$ to $L_{10}$ and a plurality of columns $C_1$ to $C_{10}$. In FIGS. 1 and 4, only some of the optotypes have been shown in order not to obscure the drawings. In fact there is an optotype at each intersection between a row and a column.

Each column has optotypes perceived by the human eye as having the same contrast. The first column $C_1$ has a contrast perceived as being the maximum, and each following column has a contrast perceived as decreasing up to the final column $C_{10}$, the perceived contrast of which is the minimum. This minimum perceived contrast corresponds to the minimum contrast perceived by a healthy subject. This contrast value was obtained by means of clinical tests. The decrease in contrast between columns $C_1$ and $C_{10}$ is logarithmic, in order to follow the natural perception of contrasts in humans.

The contrast within any one column is not strictly identical for each of the optotypes, even if it is perceived by the human eye as being identical. In fact, the contrast of each of the optotypes in any one column is determined in such a way that the human eye perceives it as being virtually identical, but each of the contrast values in any one column is different.

In order to determine the true contrast values, it is necessary to take account of the fact that the contrast value of an optotype depends on its size, ie its spatial frequency. For each letter used it is also necessary to take account of the size of the detail (in this letter) which makes it possible to recognise the letter. Therefore for each letter, and according to the size of the recognition detail in each letter, it is possible to determine a density (a contrast) such that the human eye perceives two letters of different sizes and whose true contrast in terms of density will in fact be different, as having identical contrasts.

Such columns are defined as having isosensitivity to spatial contrasts in humans. The test equipment according to the invention thus has ten columns of isosensitivity to spatial contrasts. In each of these columns, the contrast value of the optotypes also follows the curve for contrast sensitivity in humans, which enables the human eye to perceive them as having the same contrast.

Thus the column with the lowest perceived contrast has, as contrast values for each of the optotypes composing it from the first to the last row, the following values: for rows $L_1$ and $L_2$ the contrast is from 2.0% to 3.0% with respect to the background on which the letters appear, for rows $L_3$ and $L_4$, 3.1% to 3.5%, for rows $L_5$ and $L_6$, 3.6% to 4.0% for rows $L_7$ and $L_8$, 4.1% to 5.0% and for rows $L_9$ and $L_{10}$, 5.1% to 6.5%.

The preceding columns increase each of these contrast values logarithmically. Table 1 will be found below, recapitulating for each column 1 to 10 and each row 1 to 10 the contrast of the in optotypes expressed as a percentage with respect to the background, ie the rest of the sheet supporting the optotypes.

| Row | Column | | | | | | | | | |
|---|---|---|---|---|---|---|---|---|---|---|
|  | 1 | 2 | 3 | 4 | 5 | 6 | 7 | 8 | 9 | 10 |
| 1 and 2 | 95–100 | 26–30 | 18–21 | 12–15 | 7–10 | 5.1–6.5 | 4.1–5.0 | 3.6–4.0 | 3.1–3.5 | 2.0–3.0 |
| 3 and 4 | 95–100 | 32–36 | 22–25 | 13–21 | 12–15 | 7–10 | 5.1–6.5 | 4.1–5.0 | 3.6–4.0 | 3.1–3.5 |
| 5 and 6 | 95–100 | 38–41 | 26–30 | 22–25 | 18–21 | 12–15 | 7–10 | 5.1–6.5 | 4.1–5.0 | 3.6–4.0 |
| 7 and 8 | 95–100 | 44–48 | 32–36 | 26–30 | 22–25 | 18–21 | 12–15 | 7–10 | 5.1–6.5 | 4.1–5.0 |
| 9 and 10 | 95–100 | 50–55 | 38–42 | 32–36 | 26–30 | 22–28 | 18–21 | 12–15 | 7–10 | 5.1–6.5 |

Rows $L_1$ to $L_{10}$ have optotypes with a given spatial frequency which advantageously corresponds with the spatial frequencies used for the acuity tests.

Thus the spatial frequencies increase from the first row $L_1$ to the last $L_{10}$ and are as follows: 3; 6; 9; 12; 15; 17.5; 20; 24; 27 and 30 cycles per degree. These spatial frequencies correspond respectively to those used to determine the following degrees of acuity: 1/10; 2/10; 3/10; 4/10; 5/10; 6/10; 7/10; 8/10; 9/10; and 1.

It will be recalled that the spatial frequency of an optotype is defined as being the reciprocal of the dimension of the detail of the optotype expressed in degrees (since it is seen at a certain distance and at a certain angle) and is expressed in cycles per degree.

The equipment thus described is intended to be placed on a device 20 for determining visual acuity and/or visual sensitivity to spatial contrasts in humans, described below.

This device includes in particular a support means 21, illumination means 22 and the test equipment 10.

The support means 21 (FIG. 3) consists of a parallelepipedal box having a rear face 23, a front face 24, top and bottom faces 25, 26 and two lateral faces 27 and 28 (FIG. 1). A cover 29 fits onto the periphery of the front face 24 of the box. This cover is fixed to the top face of the box by a hinge 30 and is held against the bottom face 26 of the box by a retaining device 31. The front face 24 of the box 21 is divided into two separate areas, a first part consisting of a diffusing plate 32 (FIG. 3) and a second part consisting of a control panel 33 (FIG. 1). The test equipment according to the invention is placed against the diffusing part 32 (FIG. 3) so that the optotypes which it contains are legible from outside the box. A glass plate 50 treated so as to be non-reflecting is pressed against the diffusing face 32 so that the test equipment is held between the diffusing plate 32 and the treated glass 50. A silicone bead 51 is placed all around the glass plate 32 so as to adhere to each of these two plates 32 and 50. This bead 51 thus extends over the entire periphery of the plates, except at one point through which the air trapped between the plates 32 and 50 is sucked out, so that a vacuum is created between these two plates. The silicone joint is then closed again. Such a joint ensures on the one hand that no air bubble is present between the plates 32 and 50 and on the other hand that no dust or contamination can enter between these two plates 32 and 50. Good resistance to ageing of the assembly is thus ensured.

The illumination means 22 is housed inside the box and consists of a light source including at least four neon tubes 34.

These neon tubes are supplied with power by means of an electronic unit 35, itself controlled by a selector means 36. This selector means is equipped in particular with three selector buttons 38. A power supply unit supplies the power required by the selector means and electronic unit in order to operate. This power supply unit is equipped with an off/on switch 37. The operation of this device is described below.

Once the switch 37 has been put in the on position, the selector means and electronic unit are supplied with power. The practitioner presses one of the selector buttons 38. The selector means then sends a selector signal to the electronic unit, making it supply the neon tubes at a certain power level, so that the illumination means illuminates the diffusing face 24 according to a given preestablished luminosity.

Preferably, the selector means provides three possible choices of luminosity, each one associated with one of the buttons 38. A first luminosity level, known as the mesopic level, produces illumination of the diffusing face of the box at a value of about 3 to 10 cd/m$^2$. Such illumination corresponds to twilight.

A second luminosity level corresponds to the medium light level of a day without direct sunlight, and produces illumination of the diffusing face 32 of about 80 to 90 cd/m$^2$.

A third luminosity level corresponds to the light level on a very sunny day and produces illumination on the diffusing face of the box of 600 to 1000 cd/m$^2$.

The selector means has in addition a remote-control device 40 enabling the signal selecting the chosen luminosity to be sent by means of infrared radiation to an infrared receiver 41 associated with the electronic unit.

The control panel 33 is also equipped with a voltage on/off indicator 42.

When the practitioner has chosen the illumination of the diffusing face, either directly by the selector means 36, or by infrared remote control, the illumination means illuminates the diffusing sheet uniformly according to the illumination level chosen.

The practitioner then gets his patient to read the letters appearing on the diffusing face. He may, for this purpose, use a laser pointer to show his patient which are the letters to be read. If necessary, this test can be carried out with the other luminosity values. Of course, the minimum contrasts perceived by a healthy subject depend on the luminosity of the diffusing face. For a luminosity of 80 to 90 cd/m$^2$, it is the last column of the test equipment which contains the minimum contrasts perceived by a healthy subject. For the other luminosity values of the diffusing face, these minimum values are found on each row of the test equipment. Once the test is finished, the practitioner switches off the power supply to the device.

It should of course be noted that no graph or additional analysis is necessary for the practitioner in order to establish a diagnosis concerning a possible pathological condition in the eye.

Such a device therefore affords easy, rapid and systematic screening for any abnormality in the perception of spatial contrasts, and this because the last column $C_{10}$ immediately gives the minimum contrast perceived by a healthy subject as a function of each spatial frequency. Thus, if the patient succeeds in reading the last column, the practitioner knows immediately that his sensitivity to contrasts is not abnormal. If on the other hand the patient can read only as far as minus one or minus two columns of $C_{10}$, this means that his sensitivity to contrasts is reduced. In addition, the practitioner knows immediately that this patient's sensitivity to contrast is $C_9$ or $C_8$. No graph is necessary to study the performance of each patient in comparison with the performance of a healthy subject.

It should be noted that a simple reading of the column with the highest contrast enables a traditional acuity test to be carried out. Such test equipment therefore enables visual acuity and/or sensitivity to spatial contrasts to be determined.

As a variant, the device according to the invention is equipped with more than four neon tubes in order to obtain higher illumination levels, or even to carry out this same contrast sensitivity test in dazzling light.

Also as a variant, the test equipment according to the invention may have all kinds of optotypes, letters, figures, symbols or images, the latter in particular in order to carry out a test for sensitivity to spatial contrasts on children and illiterates.

Also as a variant and as shown in FIG. 4, it may prove necessary to carry out a contrast test for a level of visual acuity below 1/10 and in particular for a level of acuity of 1/20. In that case the corresponding optotypes are larger than those in row 1/10 and are not contained in one test row.

According to this variant embodiment, this supplementary row is divided between a first row LO and an eleventh column surrounding the previously described optotypes of the contrast test equipment. This makes it possible to use the available space advantageously for the test equipment without increasing it in order to add this supplementary row which is sometimes necessary. In this way, neither the dimensions nor the weight nor the cost of the equipment is increased.

It should also be noted that in some countries, certain intermediate (such as 1.5/10), or higher (such as 12/10), acuities are tested. In this case, a row, the spatial frequency of which corresponds to this acuity, is added to the table of optotypes.

The method of producing equipment according to the invention is described hereafter.

In order to produce the equipment according to the invention:

- by means of a central computing unit, optotypes of a size determined so as to confer on them a specific spatial frequency are created,
- the optotypes of a given size are given a density determined so as to confer on them a specific contrast value,
- all the optotypes of the same spatial frequency are arranged in the same row or the same column,
- all the optotypes perceived by a person as having the same contrasts are arranged in the same column or the same row,
- the table of optotypes thus created is displayed on a screen associated with the central unit,
- a positive of the screen is produced on a photosensitive film, a negative of the positive is produced, the said negative is printed by means of a photographic process, the contrast of each of the optotypes appearing on the print is verified, the optimum exposure times for the negative in order to obtain the required contrasts are derived therefrom, and the said negative is printed by means of a photographic process in order to produce a plurality of identical items of equipment for testing visual acuity and/or contrasts.

Such a manufacturing process enables the production of the test equipment according to the invention to be rigorously controlled.

The homogeneity and quality of the test equipment are thus guaranteed (particularly as far as the contrast values of each optotype are concerned).

Advantageously, the final printing is carried out on a transparent or translucent film; any ageing such as appears in particular with the positive produced is avoided.

It should however be noted that the test equipment according to the invention can also be produced on an opaque sheet.

Of course, the present invention is not limited to the embodiment described above and includes any variant within the range of a person skilled in the art.

Thus the test equipment according to the invention may be produced in black and white or in colour.

In addition, the role of the rows and columns of the test according to the invention may be reversed without, for all that, departing from the scope of the invention. Thus it is entirely possible to create rows of isosensitivity to spatial contrasts, and columns each with the same spatial frequency.

Likewise, the contrast test equipment according to the invention may be produced on a film which is then projected onto a surface, the luminosity of which is controlled.

The spatial frequency values explored by the contrast test according to the invention may be other than those previously indicated. Likewise, the perceived contrast values explored may include sets of optotypes, the perceived contrast of which is lower than the minimum perceived by a healthy subject.

Nor is it necessary to carry out the present test with 10 rows and 10 columns. In fact, this test may include any number of rows and columns, and different numbers thereof.

Similarly, the light source used in the device according to the invention may consist of a single neon tube (or of several) coiled inside the box rather than rectilinear.

In addition this light source may be produced with fluorescent tubes or other equivalent means. The aim here is to produce uniform illumination of the diffusing face 32.

I claim:

1. Equipment for testing visual acuity and/or visual sensitivity to spatial contrasts in humans, comprising:

a) a sheet having a plurality of optotypes disposed on one of its faces, said optotypes being distributed in rows $L_1 \ldots L_N$ and columns $C_1 \ldots C_N$;

b) said optotypes having the same spatial frequency are arranged in the same row $L_1 \ldots L_N$, said spatial frequency increasing from the first row $L_1$ to the last row $L_N$, said spatial frequency corresponding with the spatial frequency used for acuity tests;

c) said optotypes constituting contrast isosensitivity sets are arranged in columns $C_1 \ldots C_N$, and the luminance contrast of which has values decreasing from a first column $C_1$, with a maximum contrast value, to a last column $C_n$, with a minimum contrast value; and d) said N is an integer.

2. Equipment as in claim 1, wherein:
said contrast values decrease logarithmically from one column to the next.

3. Equipment as in claim 1, wherein:
said $N = 10$ whereby said rows and columns comprise 10 rows and 10 columns.

4. Equipment as in claim 3, wherein:
said last column $C_{10}$ has the following luminance contrast values, expressed as a contrast percentage with respect to the background on which said optotypes are produced: for rows $L_1$ and $L_2$ a contrast of 2.0 to 3.0%, for rows and $L_3$ and $L_4$, 3.1 to 3.5%, for rows $L_5$ and $L_6$, 3.6 to 4.0%, for rows $L_7$ and $L_8$, 4.1 to 5.0%, and for rows $L_9$ and $L_{10}$, 5.1 to 6.5%.

5. Equipment as in claim 3, wherein:
said spatial frequency of each of the rows $L_1$ to $L_{10}$ corresponds respectively to the following values: 3; 6; 9; 12; 15; 17.5; 20; 24; 27 and 30 cycles per degree.

6. Equipment as in claim 3, wherein:
each of said rows $L_1$ to $L_{10}$ corresponds, when seen from a predetermined distance, respectively to the following degrees of visual acuity: 1/10; 2/10; 3/10; 4/10; 5/10; 6/10; 7/10; 8/10; 9/10; 1.

7. Equipment as in claim 1, wherein:
said optotypes are letters.

8. Equipment as in claim 1, wherein:
said optotypes are images designed so as to be recognizable by children or illiterates.

9. Equipment as in claim 1, wherein:
said sheet is translucent.

10. Equipment as in claim 1, wherein:
a) said rows are eleven rows, $L_0$ to $L_{10}$; and
b) said optotypes having lowest spatial frequency are distributed over a first row $L_0$ and an eleventh column $C_{11}$.

11. Testing equipment for determining human visual sensitivity to contrasts, comprising:

a) a sheet having a plurality of optotypes disposed on one of its faces, said optotypes being distributed in rows $L_1 \ldots L_{10}$ and columns $C_1 \ldots C_{10}$;

b) said optotypes having the same spatial frequency are arranged in the same row $L_1 \ldots L_{10}$, said spatial frequency increasing from the first row $L_1$ to the last row $L_{10}$, said spatial frequency corresponding with the spatial frequency used for acuity tests;

c) said optotypes constituting contrast isosensitivity sets are arranged in columns $C_1 \ldots C_{10}$, and the luminance contrast of which has values decreasing from a first column $C_1$, with a maximum contrast value, to a last column $C_{10}$, with a minimum contrast value;

d) support means having a diffusing front face, said sheet being disposed on said front face; and e) an illumination means housed inside said support means and adapted for illuminating uniformly, according to a predetermined luminosity, said front face of said support means.

12. Testing equipment as in claim 11, wherein:

said last column $C_{10}$ has the following luminance contrast values, expressed as a contrast percentage with respect to the background on which said optotypes are produced: for rows $L_1$ and $L_2$ a contrast of 2.0 to 3.0%, for rows and $L_3$ and $L_4$, 3.1 to 3.5%, for rows $L_5$ and $L_6$, 3.6 to 4.0%, for rows $L_7$ and $L_8$, 4.1 to 5.0%, and for rows and $L_9$ and $L_{10}$, 5.1 to 6.5%.

13. Testing equipment as in claim 11, wherein:

said sheet is translucent.

14. Testing equipment as in claim 11, and further comprising:

means for selecting the luminosity of said illumination means.

15. Testing equipment as in claim 14, wherein:

said selection means is adapted for allowing a choice between at least three distinct luminosity levels, a low luminosity level, a medium luminosity level and a high luminosity level.

16. Testing equipment as in claim 15, wherein:

said selection means is adapted for causing illumination of said diffusing face of said support means of around 3 to 30 cd/m², 80 to 90 cd/m² and 600 to 1000 cd/m² to correspond respectively to said low, medium and high luminosity levels.

17. Testing equipment as in claim 14, wherein:

said selection means is a device integrated into said support means.

18. Testing equipment as in claim 14, wherein:

said selection means is an infrared remote-control device.

19. Testing equipment as in claim 14, wherein:

said selection means includes an electronic unit adapted for controlling the intensity of the current delivered to said illumination means according to the luminosity selected.

20. Testing equipment as in claim 11, wherein:

said illumination means comprises a plurality of uniformly distributed light sources.

21. Testing equipment as in claims 20, wherein:

said plurality of light sources comprises at least four neon tubes.

22. Process for manufacturing equipment for testing visual acuity and/or sensitivity to contrasts, comprising the steps of:

a) creating, by means of a central computing unit, optotypes of a size determined so as to confer on them a specific spatial frequency;

b) giving the optotypes of a given size a density determined so as to confer on them a specific contrast value;

c) arranging all the optotypes of the same spatial frequency in the same row;

d) arranging the optotypes in columns, which have a luminance contrast with values decreasing from a first column $C_1$ with a maximum contrast value, to a last column $C_{10}$ with a minimum contrast value;

e) displaying the table of optotypes thus created on a screen associated with the central computing unit;

f) producing a positive of the screen on a photosensitive film;

g) producing a negative of the positive;

h) printing the negative by means of a photographic process;

i) verifying the contrast of each of the optotypes appearing on the print;

j) deriving therefrom the optimum exposure times for the negative in order to obtain the required contrasts; and, k) printing the negative by means of a photographic process.

23. Process as in claim 22, wherein: the contrast is verified so as to obtain a last column $C_{10}$ having the following luminance contrast values, expressed as a contrast percentage with respect to the background on which the optotypes are produced: for rows $L_1$ and $L_2$ a contrast of 2.0 to 3.0%, for rows and $L_3$ and $L_4$, 3.1 to 3.5%, for rows $L_5$ and $L_6$, 3.6 to 4.0%, for rows $L_7$ and $L_8$, 4.1 to 5.0%, and for rows $L_9$ and $L_{10}$, 5.1 to 6.5%.

24. Process as in claim 22, wherein:

the first row $L_1$ of the optotypes in the table is arranged so that it includes the optotypes with the lowest spatial frequency and the following rows $L_2$ to $L_{10}$ are arranged in higher and higher spatial frequencies.

25. Process as in claim 22, wherein:

the negative is printed on a transparent or translucent sheet.

* * * * *